United States Patent [19]
Onopchenko et al.

[11] 3,978,143
[45] Aug. 31, 1976

[54] PROCESS FOR PREPARING DIARYLDINITROETHYLENES

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: May 27, 1975

[21] Appl. No.: 581,087

[52] U.S. Cl. .................................. 260/645; 260/591
[51] Int. Cl.² ........................................ C07C 79/10
[58] Field of Search ....................................... 260/645

[56]  References Cited
OTHER PUBLICATIONS

Anschutz et al., Ber. Deut. Chem., vol. 54, pp. 1854 to 1859 (1921).

Wieland et al., Ber. Deut. Chem., vol. 54, pp. 1770 to 1779 (1921).

Primary Examiner—Leland A. Sebastian

[57]  ABSTRACT

A process for converting a 1,1-bis(alkylphenyl)ethane to the corresponding novel 1,1-bis(alkylphenyl)-2,2-dinitroethylene which involves heating a mixture containing critical amounts of 1,1-bis(alkylphenyl)ethane, nitric acid and water.

10 Claims, No Drawings

PROCESS FOR PREPARING DIARYLDINITROETHYLENES

FIELD OF THE INVENTION

The invention herein relates to the conversion of a 1,1-bis(alkylphenyl)ethane to the corresponding 1,1-bis(alkylphenyl)-2,2-dinitroethylene and to 1,1-bis(alkylphenyl)-2,2-dinitroethylenes as new compounds.

DESCRIPTION OF THE PRIOR ART

U.S. Pat. No. 3,075,007 to McCracken et al. discloses a process wherein a diarylalkane is subjected to oxidation with nitric acid to obtain a diarylketone, particularly a diarylketone polycarboxylic acid. U.S. Pat. No. 3,479,400 to Lese et al. discloses a process wherein a diarylalkane is subjected to oxidation with nitric acid in a first stage to obtain oxidation products of the diarylalkane, the oxidation products so obtained are further subjected to oxidation with additional nitric acid to obtain a diarylketone carboxylic acid and using the resulting nitric acid as oxidant in the initial oxidation. In U.S. Pat No. 3,641,132 to Schulz et al., nitric acid is added to a diarylalkane to obtain a nitro benzophenone. R. Anschutz and A. Hilbert in *Berichte der Deutschen Chemischen Gesellschaft*, Volume 54, pages 1854–1859 (1921) report the formation of 1,1-diphenyl-2,2-dinitroethylene as a result of the addition of nitric acid to 1,1-diphenylethylene, but do not report any of its physical properties or specific experimental details. In fact, while the compound alleged to be formed is identified as 1,1-diphenyl-2,2-dinitroethylene, the authors make it clear in the text that they have no idea of its structure and are simply referring to it as a "dinitrite". In any event, the German authors found the major product resulting from the reaction of olefin with nitric acid to be the corresponding nitroalcohol, some nitroolefin, and only small amounts of the dinitroolefin. On pages 1770–1779 of the same volume, H. Wieland and F. Rahn report on the preparation of 1,1-diphenyl-1,2-dinitroethane from 1,1-diphenylethylene as well as the conversion of the 1,2-dinitroalkane bridge to mononitroolefin. The authors suggest that reaction of 1,1-diphenylethylene with nitric acid to form nitroalcohol is so fast that all traces of water must be completely eliminated for the addition of the two nitro groups to occur.

SUMMARY OF THE INVENTION

The process defined and claimed herein relates to a procedure wherein a mixture containing critical amounts of 1,1-bis(alkylphenyl)ethane, nitric acid and water are heated to obtain the corresponding 1,1-bis(alkylphenyl)-2,2-dinitroethylenes. The latter are also claimed as novel compounds.

BRIEF DESCRIPTION OF THE PROCESS

Into a stirred reactor there is introduced a 1,1-bis(alkylphenyl)ethane, nitric acid and water. The 1,1-bis(alkylphenyl)ethane can be represented by the following structural formula:

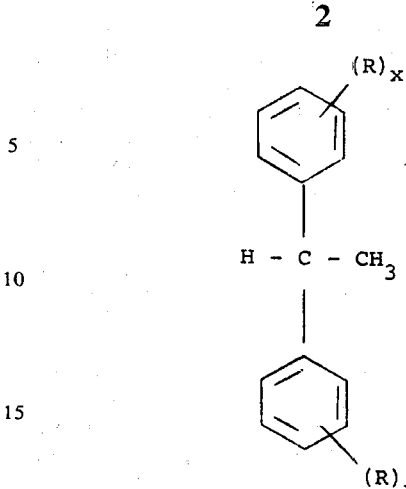

wherein each R is an alkyl substituent, the same or different, having from one to 10 carbon atoms, preferably from one to two carbon atoms, and $x$ is an integer having a value of from 1 to 4, preferably from 1 to 2. Examples of compounds that can be used include 1,1-bis(p-tolyl)ethane,
1,1-bis(m-tolyl)ethane,
1,1-bis(o-tolyl)ethane,
1,1-bis(2,3-dimethylphenyl)ethane,
1,1-bis(3,4-dimethylphenyl)ethane,
1,1-bis(2,4-dimethylphenyl)ethane,
1,1-bis(2,5-dimethylphenyl)ethane,
1,1-bis(2,6-dimethylphenyl)ethane,
1,1-bis(3,4-diethylphenyl)ethane,
1,1-bis(2,3-diethylphenyl)ethane,
1,1-bis(4-ethylphenyl)ethane,
1,1-bis(3-ethylphenyl)ethane,
1-(3,4-dimethylphenyl)-1-(3,4-diethylphenyl)ethane,
1-(2,3,5-trimethylphenyl)-1-(2-ethyl-4-propylphenyl)ethane and mixtures thereof. Of these we prefer to employ 1,1-bis (4-methylphenyl)ethane and 1,1-bis (3,4-dimethylphenyl)ethane. Diarylalkanes of different structure cannot be converted to the desired diphenyldinitroethylene in accordance with this process. Only substrates with an ethylidene bridge

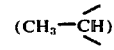

will produce dinitroolefins. The simplest 1,1-diarylalkane has a methylene bridge ($-CH_2-$) which on reaction with nitric acid is converted to carbonyl. 1,1-Diarylalkanes wherein the bridging alkyl group has more than two carbons form only mononitroolefins. The present process is therefore uniquely applicable to 1,1-diarylethanes.

The amounts of nitric acid introduced into the reaction zone can be varied over a wide range but are so correlated that the resultant total amounts of each will result in an aqueous nitric acid solution having a concentration of about 30 to about 90 weight percent, preferably about 40 to about 75 weight percent. The molar amount of nitric acid employed, determined as 100 percent nitric acid, relative to the mols of 1,1-bis(alkylphenyl)ethane must be in the range of about 3:1 to about 20:1, preferably about 4:1 to about 10:1. In order to assure that sufficient amount of the desired diphenyldinitroethylene will be obtained, and that no appreciable oxidation of any of the nuclear alkyl substituents to carboxyl groups takes place, it is critical that the relative amounts of the 1,1-bis(alkylphenyl)ethane, nitric acid and water introduced into the reaction zone be within well-defined limits. These limits arbitrarily designated as nitric acid parameter can be determined by multiplying the ratio of the absolute mols of nitric acid to the mols of 1,1-bis(alkylphenyl)ethane times the concentration of the nitric acid in weight percent:

$$\text{Nitric Acid Parameter} = \left(\begin{array}{c}\text{Concentration of HNO}_3\\ \text{in weight percent}\end{array}\right)\left(\begin{array}{c}\text{Mols of HNO}_3\\ \overline{\text{Mols of 1,1-bis-}}\\ \text{(alkylphenyl)ethane}\end{array}\right),$$

We have found that when the numerical product of the above is above 150 and up to about 1000, preferably in the range of about 300 to about 750, a large amount of the desired 1,1-bis(alkylphenyl)-2,2-dinitroethylene is obtained, but no appreciable conversion of the nuclear alkyl substituents takes place. As shown in our copending Application Ser. No. 581,287 filed concurrently herewith, when the numerical product of the above is 150 and below, the amount of desired diphenyldinitroethylene is substantially reduced and very large amounts of alkylbenzophenone are obtained instead.

The temperature of the reaction can be in the range of about 30° to about 125° C., preferably about 60° to about 100° C., the pressure about atmospheric to about 500 pounds per square inch gauge (about atmospheric to about 35 kilograms per square centimeter) preferably at atmospheric pressure, and the residence time about 1 minute to about 24 hours, preferably about 5 minutes to about 4 hours.

The reaction product obtained under the above reaction conditions will contain in general, about 0 to about two weight percent unreacted 1,1-bis(alkylphenyl)ethane, about 40 to about 80 weight percent of the desired 1,1-bis(alkylphenyl)-2,2-dinitroethylene, about 5 to about 20 weight percent 1,1-bis(alkylphenyl)-2-mononitroethylene and about 15 to about 60 percent by weight of alkylbenzophenone with consumption of stoichiometric amounts of nitric acid.

Recovery of the desired diphenyldinitroethylene from the reaction product can be effected in any desired manner. When the organic phase is in the form of a heavy liquid it can be separated from the aqueous phase by decantation. When the organic phase is crystalline, separation can be effected by filtration. The aqueous phase will contain water and spent nitric acid, while the organic phase will contain the remaining components defined above. An especially effective means for recovering the desired diphenyldinitroethylene is to recrystallize the same from methanol or some other common solvent. The organic product is dissolved in methanol to make a 5 to 50 percent solution which is warmed to a temperature of about 40° to about 60° C. for about 5 to about 60 minutes and then cooled to room temperature. The resulting crystalline material is the desired diphenyldinitroethylene, which can be recovered by filtration. If the filtrate is further concentrated crystalline alkylbenzophenone will be obtained which can also be recovered by filtration. The residue which predominates in mononitroethylene can be recovered by distillation or crystallization.

The 1,1-bis(alkylphenyl)-2,2-dinitroethylene are novel compounds and are claimed as such herein. They can be used as starting materials for conversion to the corresponding benzophenone carboxylic acids through oxidation. Their uses lie in the area of polyester fibers and plastics. These are especially desirable for the preparation of the corresponding benzophenones which are also useful as photosensitizers and drug intermediates. Thus by merely heating the diphenyldinitroethylene in the presence of water to a temperature of about 150° to about 250° C. and autogeneous pressure for about 15 to about 120 minutes and then cooling to room temperature will result in the formation of the crystalline alkylbenzophenone, which can easily be recovered by filtration.

DESCRIPTIONS OF PREFERRED EMBODIMENTS

Example I

A mixture consisting of 58 grams of 1,1-bis(3,4-dimethylphenyl)ethane (DXE) was mixed with 150 grams of water and 204 grams of 70 percent aqueous nitric acid and slowly heated while stirring to 90° C. Based on the total amount of water and nitric acid present, the initial concentration of the nitric acid in the reaction zone was 40 percent. The molar ratio of nitric acid (as 100 percent nitric acid) to DXE was 9.2:1. The product of the concentration of the nitric acid (40) and of the molar ratio of nitric acid to the diarylalkane charge (9.2:1) was therefore 368. As the temperature approached 70° C., copious amounts of brown fumes were given off, indicating that reaction had started. Reaction was continued for an additional 3 hours while maintaining an average temperature of 95° C. at atmospheric pressure. The reaction mixture was allowed to come to room temperature overnight, resulting in the formation of an aqueous solution containing a yellow heavy liquid. The aqueous phase was separated by decantation, and the organic layer was washed with about an equal volume of water. The yellow organic liquid was taken up in 300 milliliters of acetone, dried over magnesium sulfate, filtered and evaporated to dryness. Chromatographic analysis of the product (69.3 grams) showed the presence of 1.2 weight percent unreacted DXE, 42.6 weight percent 3,4,3', 4'-tetramethylbenzophenone (TMB), 11.5 weight percent 1,1-bis (3,4-dimethylphenyl)-2-nitroethylene (nitroethylene), 32.4 weight percent 1,1-bis(3,4-dimethylphenyl)-2,2-dinitroethylene (dinitroethylene), and 12.3 weight percent unidentified compounds.

Example II

The run of Example I was repeated with 60 grams of DXE, 120 grams of nitric acid and no water. The effective nitric acid concentration was therefore 70 percent and the molar ratio of nitric acid to DXE was 5.3. The product of the concentration of nitric acid and of the molar ratio of nitric acid to diarylalkane was 371. The reaction time was two hours and the temperature was maintained in the range of 90° to 95° C. Analysis of the product by chromatography showed the presence of 1.5 weight percent unreacted DXE, 26.0 weight percent TMB, 18.7 weight percent nitroethylene and 53.8 weight percent dinitroethylene. To recover the desired dinitroethylene from the reaction product, the organic layer (72.1 grams) was combined with 250 milliliters of methanol, heated to 50° C. and maintained at this temperature for 30 minutes and then cooled. The first product to crystallize out of solution was recovered by filtration (36 grams) and shown to be 1,1-bis(3,4-dimethylphenyl)-2,2-dinitroethylene on the basis of the following data. The dinitroethylene was a yellow-green solid having a melting point of 162°–165° C. and was completely soluble in common organic solvents, such as dimethylformamide, methanol, acetone, chloroform, dimethylsulfoxide, ethyl acetate, carbon tetrachloride, carbon disulfide and benzene. Elemental analysis showed the sample to contain 66.7 weight percent carbon and 5.67 weight percent hydrogen, as compared to calculated values of 66.30 and 5.56 weight percent, respectively. Infrared analysis in Nujol showed bands at 1522, 1372 cm⅛¹ for the nitro groups and 1636 cm$^{-1}$ for the olefinic double bond. Nuclear magnetic resonance in $CCl_4$ solvent showed peaks at 2.3 ppm (doublet, 12 protons) for the ring methyl groups, and multiplet peaks at 6.8–7.3 ppm (6 protons) for the aromatic ring protons. Data thus far considered would be consistent with the two structures A and B, below.

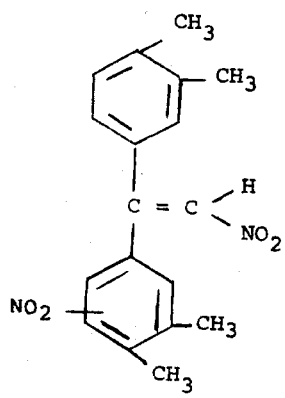
(A)

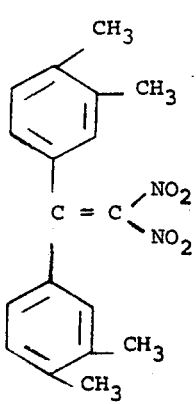
(B)

Gas chromatographic analysis favored structure B (one sharp peak), while several peaks were expected for structure A, since the nitro group on the ring could be located in several different positions. To differentiate between structures A and B, two experiments were performed. In one, the product in question was reacted with water at 200° C. for one-half hour to obtain 3,4,3′,4′-tetramethylbenzophenone, whose melting point and physical properties were found to be in agreement with the literature data.

Example III

In another experiment, 20 grams of the compound in question was heated, while stirring, with 200 grams of 33 percent aqueous nitric acid at a temperature of 170° C. for 2 hours to obtain 3,4,3′,4′-benzophenone tetracarboxylic acid, a known compound. The acid produced was found to have the same retention time as a known sample of acid, a neutral equivalent of 93–95 (theoretical 89.6), and elemental analysis of 57.4 weight percent carbon (theoretical 57.00), 2.98 weight percent hydrogen (theoretical 2.81), and 0.1 weight percent nitrogen (theoretical 0.00). Sequentially, 3,4,3′,4′-tetramethylbenzophenone (16.9 grams), a known compound, and 1,1-bis(3,4-dimethylphenyl)-2-nitroethylene were also crystallized out of solution of Example II product and analyzed. The structure of 1,1-bis(3,4-dimethylphenyl)-2-nitroethylene was based on its infrared spectrum (1634 cm$^{-1}$, olefin band; 1527, 1370 cm$^{-1}$, —$NO_2$ group), nuclear magnetic resonance spectrum (2.2 ppm, singlet, 12 protons, methyl groups; 6.9–7.3 ppm multiplet, 7 protons, ring and olefinic protons), and the mass spectral molecular weight determination (m/e = 281.1415; theoretical value, calculated for $C_{18}H_{19}NO_2$ = 281.1416). Elemental analysis for carbon and hydrogen were consistent with the expected values. The mononitroolefin herein is a yellow solid with a melting point of 96° to 99° C.

Example IV

In this example, we show that 1,1-bis(3,4-dimethylphenyl)-2,2-dinitroethylene can be converted to 3,4,3′,4′-tetramethylbenzophenone, a known compound useful in preparation of amines, as photochemical sensitizers and, as shown above, as a reactant with nitric acid to produce 3,4,3′,4′-benzophenone tetracarboxylic acid. Thus, 27 grams of 1,1-bis(3,4-dimethylphenyl)-2,2-dinitroethylene were heated with 300 grams of water at 150° C. for 2 hours and then at 200°C. for one-half hour. The product was cooled to room temperature and the recovered crystalline material was found to contain 90 weight percent 3,4,3′,4′-tetramethylbenzophenone. If desired, the total initial product of the reaction can be heated with water to convert the dinitroolefin to the corresponding benzophenone and the total benzophenone in the product can then be recovered. This is shown below.

Example V

The product of Example I (61 g.) was transferred to the autoclave and heated with 300 grams of water at 150° C. for 1 hour. After recovery of the product in a conventional manner, the latter was analyzed. Analysis showed an increase in the TMB content from 42.6 percent to 55.1 percent, and a decrease in the dinitroethylene content from 32.4 percent to 25.9 percent. It is apparent that longer reaction time will be required to convert the dinitroethylene to benzophenone, or that higher temperatures should be employed. Accordingly, 52.8 g. of the above product was heated with 270 grams of water at 200° C. for 2 hours. Analysis showed the following composition:

| Compound | Weight Percent |
|---|---|
| TMB | 80.0 |
| Nitroethylene | 7.3 |
| Dinitroethylene | 0.4 |
| Misc. (unidentified TMB precursors) | 11.3 |
| DXE | 1.0 |

Obviously, many modifications and variations of the invention, as hereinabove set forth, can be made without departing from the spirit and scope thereof, and therefore only such limitations should be imposed as are indicated in the appended claims.

We claim:
1. A process for converting a 1,1-bis(alkylphenyl)ethane to the corresponding 1,1-bis(alkylphenyl)-2,2-dinitroethylene which comprises heating a mixture of said 1,1-bis(alkylphenyl) ethane, nitric acid and water wherein the numerical product of multiplication of the concentration of nitric acid in said mixture and the ratio of the absolute mols of nitric acid to the mols of said 1,1-bis(alkylphenyl)ethane is above 150 and up to about 1000.

2. The process of claim 1 wherein said product is in the range of about 300 to about 750.

3. The process of claim 1 wherein said mixture is heated to a temperature of about 30° to about 125° C. for about 1 minute to about 24 hours.

4. The process of claim 3 wherein said mixture is heated to a temperature of about 60° to about 100° C. for about 5 minutes to about 4 hours.

5. The process of claim 1 wherein the molar amount of nitric acid, determined as 100 percent nitric acid to the molar amount of 1,1-bis(alkylphenyl)ethane is in the range of about 3:1 to about 20:1.

6. The process of claim 5 wherein the molar amount of nitric acid, determined as 100 percent nitric acid, to the molar amount of 1,1-bis(alkylphenyl)ethane is in the range of about 4:1 to about 10:1.

7. The process of claim 1 wherein said 1,1-bis(alkylphenyl)ethane is 1,1-bis(3,4-dimethylphenyl)ethane.

8. The process of claim 1 wherein the 1,1-bis(alkylphenyl)-2,2-dinitroethylene is heated with water to obtain the corresponding 3,4,3',4'-tetramethylbenzophenone.

9. The process of claim 7 wherein the 1,1-bis(alkylphenyl)-2,2-dinitroethylene is heated with water to obtain the corresponding 3,4,3',4'-tetramethylbenzophenone.

10. The process of claim 1 wherein the organic reaction product is separated from the aqueous phase, the organic phase is heated with methanol, and the resulting mixture is cooled to crystallize 1,1-bis(alkylphenyl)-2,2-dinitroethylene and thereafter recovering said 1,1-bis(alkylphenyl)-2,2-dinitroethylene.

* * * * *